(12) United States Patent
Gamboa-Pinto et al.

(10) Patent No.: US 11,382,564 B2
(45) Date of Patent: Jul. 12, 2022

(54) MEDICAL MONITORING SYSTEM WITH A FOOT DIAGNOSTIC DEVICE

(71) Applicants: Jose Antonio Gamboa-Pinto, Diamond Bar, CA (US); Diana Rashel Valencia, Pomona, CA (US); Katia Lisbeth Avila Pinedo, Pomona, CA (US); Anh Thu Thi Tran, Pomona, CA (US); Evelyn Janet Casas, Pomona, CA (US); Melody Tran Sanchez, Pomona, CA (US); Alexander Patrick Ruper, Orange, CA (US); Sushil Bohara, Pomona, CA (US); Jia Pauline Dimaano Bragado, Pomona, CA (US); Brianna Samantha Berdin, Pomona, CA (US)

(72) Inventors: Jose Antonio Gamboa-Pinto, Diamond Bar, CA (US); Diana Rashel Valencia, Pomona, CA (US); Katia Lisbeth Avila Pinedo, Pomona, CA (US); Anh Thu Thi Tran, Pomona, CA (US); Evelyn Janet Casas, Pomona, CA (US); Melody Tran Sanchez, Pomona, CA (US); Alexander Patrick Ruper, Orange, CA (US); Sushil Bohara, Pomona, CA (US); Jia Pauline Dimaano Bragado, Pomona, CA (US); Brianna Samantha Berdin, Pomona, CA (US)

(*) Notice: Subject to any disclaimer, the term of this patent is extended or adjusted under 35 U.S.C. 154(b) by 195 days.

(21) Appl. No.: 16/235,070

(22) Filed: Dec. 28, 2018

(65) Prior Publication Data
US 2020/0205736 A1    Jul. 2, 2020

(51) Int. Cl.
*A61B 5/00*      (2006.01)
*A61B 5/0205*    (2006.01)
(Continued)

(52) U.S. Cl.
CPC .......... *A61B 5/6829* (2013.01); *A61B 5/0022* (2013.01); *A61B 5/0205* (2013.01);
(Continued)

(58) Field of Classification Search
CPC ... A61B 5/6829; A61B 5/0205; A61B 5/0022; A61B 5/742; A61B 5/7246;
(Continued)

(56) References Cited

U.S. PATENT DOCUMENTS

| | | | |
|---|---|---|---|
| 10,282,914 B1* | 5/2019 | Tran | G01G 19/44 |
| 2007/0038042 A1* | 2/2007 | Freeman | A61B 5/14552 600/310 |

(Continued)

FOREIGN PATENT DOCUMENTS

WO    WO-2017008138 A1 *    1/2017    ........... A61B 5/6891

OTHER PUBLICATIONS

Definition of correlate. Collins Dictionary, retrieved on Feb. 8, 2021; Retrieved from the Internet: <https://www.collinsdictionary.com/us/dictionary/english/correlate> (Year: 2021).*

*Primary Examiner* — Gary Jackson
*Assistant Examiner* — Sebastian X Lukjan

(57) ABSTRACT

Described herein is a monitoring system that includes a foot diagnostic device. The foot diagnostic device is shaped to receive one or both of a user's feet. The foot diagnostic device is equipped with a number of sensors that may work together or separately from each other, which are able to measure different diagnostic attributes of the feet. The system includes a mobile application and the ability to transmit information to the mobile application and other locations such as a physician's office.

12 Claims, 6 Drawing Sheets

(51) Int. Cl.
*A61L 2/10* (2006.01)
*A61B 5/026* (2006.01)
*A61B 5/1455* (2006.01)

(52) U.S. Cl.
CPC ............ *A61B 5/702* (2013.01); *A61B 5/7246* (2013.01); *A61B 5/742* (2013.01); *A61L 2/10* (2013.01); *A61B 5/0077* (2013.01); *A61B 5/026* (2013.01); *A61B 5/14551* (2013.01); *A61B 5/4041* (2013.01); *A61B 5/4519* (2013.01); *A61B 2562/066* (2013.01); *A61L 2202/24* (2013.01)

(58) Field of Classification Search
CPC ..... A61B 5/0077; A61B 5/026; A61B 5/4041; A61B 5/4519; A61B 5/14551; A61B 2562/066; A61B 5/702; A61L 2/10; A61L 2202/24; A61L 2202/11
See application file for complete search history.

(56) References Cited

U.S. PATENT DOCUMENTS

| | | | |
|---|---|---|---|
| 2007/0211355 A1* | 9/2007 | Dalbo | G01G 23/3728 359/871 |
| 2009/0030337 A1* | 1/2009 | Gozani | A61B 5/389 600/554 |
| 2009/0143842 A1* | 6/2009 | Cumbie | A61N 5/0624 607/88 |
| 2013/0035563 A1* | 2/2013 | Angelides | G06F 1/1684 600/301 |
| 2014/0288621 A1* | 9/2014 | Efremkin | A61N 5/022 607/89 |
| 2015/0342496 A1* | 12/2015 | Greiser | G01R 33/20 600/420 |
| 2017/0231490 A1* | 8/2017 | Toth | A61B 90/37 600/558 |

* cited by examiner

MEDICAL MONITORING SYSTEM WITH A FOOT DIAGNOSTIC DEVICE

BACKGROUND

Many people have medical conditions that require monitoring to determine the overall health of the patient. One such condition includes diabetes, which can lead to peripheral artery disease. If a patient experiences peripheral artery disease, blood vessels can narrow, thereby causing reduced blood flow to limbs and appendages such as the legs and feet. In severe cases, a patient may experience nerve damage to their feet. Nerve damage can be particularly dangerous because it prevents the patient from realizing that other medically dangerous conditions have occurred. For instance, wounds or ulcers may be present, but the patient may not be aware of them. In extreme circumstances, the medical conditions may deteriorate to the point of requiring amputation. As a result, monitoring of a patient's medical condition may be helpful in preventing conditions that escalate to a situation that requires amputation.

SUMMARY

The device described below will provide an exemplary overview of a diagnostic device for use with a human foot within the context of a monitoring system. The embodiments disclosed will be able to accommodate two feet, but it will be understood that the device could be used with a single foot or constructed in a manner to only accommodate a single foot at a time.

The exemplary embodiments disclosed will include an enclosure for a user's feet and will further contain a number of different sensors. The various sensors will be able to work together or separately to measure different diagnostics about a user's feet. Furthermore, the different sensors may perform diagnostic readings over time to provide a more complete picture of a patient's diagnostic condition. Furthermore, while a limited number of configurations of the sensors are shown in the exemplary embodiments discussed below, it will be understood that other suitable configurations may be used to monitor the diagnostics that will provide information on the overall health of the foot.

The device will further include an ability to collect and transmit the diagnostic information about a user's feet to other locations including a user's mobile device, or a remotely located computer, such as one located at a user's physician's office. It will be understood that such diagnostic information may be processed at other locations as previously mentioned, or may be processed and output at the device as well.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure. These and various other features may be apparent from a reading of the following Detailed Description and a review of the associated drawings.

DETAILED DESCRIPTION

Overview

Figure 1:
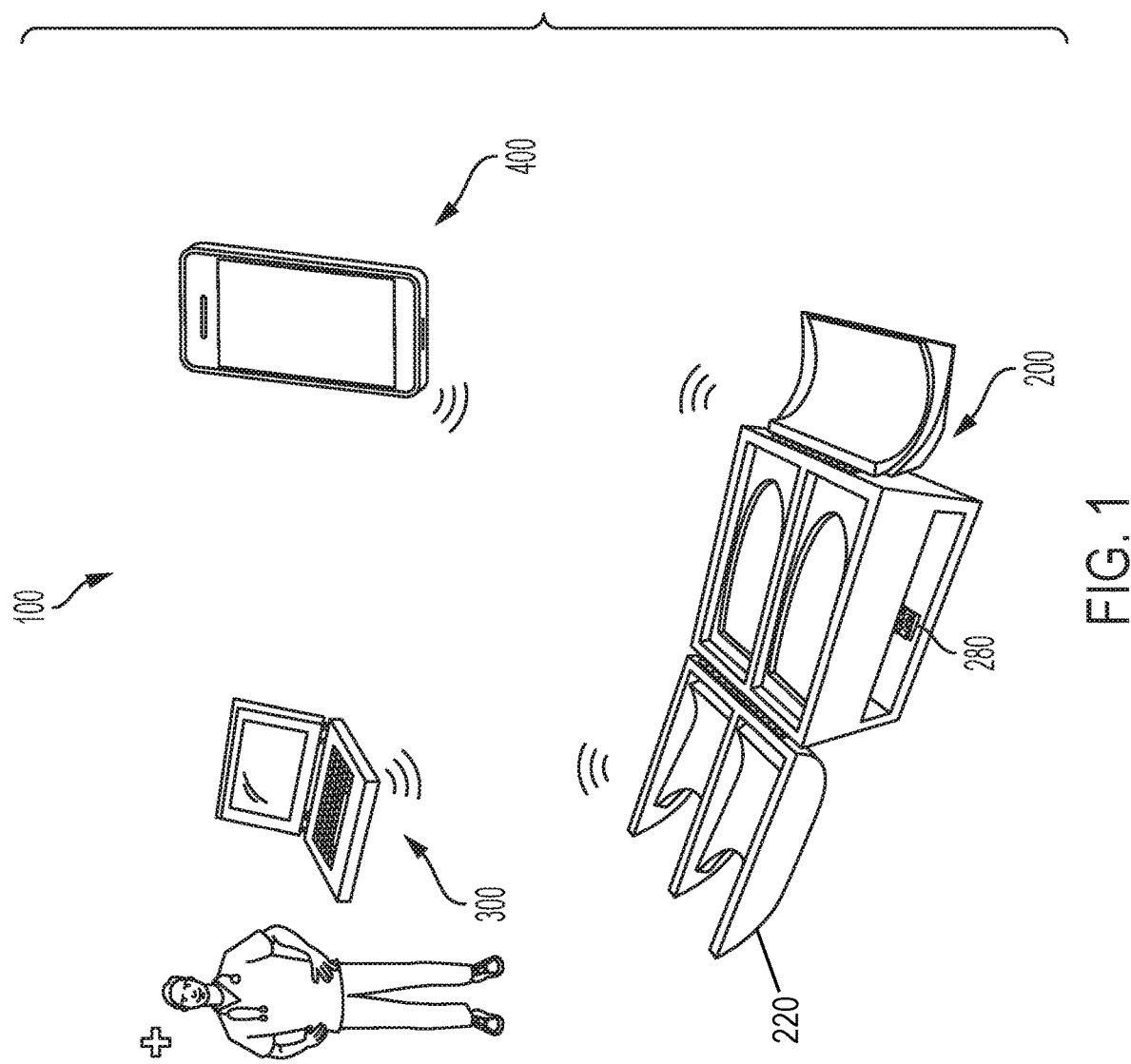
FIG. 1 shows a system view of an exemplary monitoring system.

As will be described now in further detail, FIG. 1 shows a monitoring system (100) that may be used to monitor a number of diagnostic indicators used to assess the health of a user's foot. In particular, monitoring system (100) can include a number of components such as a foot diagnostic device (200), a remote computing device (300), and a user's mobile device (400). Foot diagnostic device (200) can be used by a patient to monitor many kinds of diagnostic information that is obtained through the foot of the patient, which will be described in further detail below.

Upon obtaining diagnostic information through foot diagnostic device (200), information may be processed and sent to remote computing device (300). In some embodiments, remote computing device (300) could be located in a hospital or at the patient's primary physician's office. As a result, a patient's physician may be able to review diagnostic information and assess the health of the patient. In the event that the diagnostic information indicates that the patient's condition is deteriorating, the physician would be able to contact the patient to suggest treatment for the patient. In some embodiments, diagnostic information from foot diagnostic device (200) may be sent in real-time to a physician while in other embodiments, diagnostic information may be collected and sent in batches at a regular cadence or in an ad hoc or on-demand manner.

In some embodiments, foot diagnostic device (200) may also be used with a user mobile device (400). User mobile device (400) may include a smartphone, tablet, or any other type of mobile computing device. By using user mobile device (400), the patient can view diagnostic information transmitted from foot diagnostic device (200) to user mobile device (400). In some variations, the patient can use user mobile device (400) to also initiate some of the diagnostic tests capable of being performed by foot diagnostic device (200). User mobile device (400) could also receive information from diagnostic tests in a real-time manner or through a batch or ad hoc process.

In any of the embodiments described, it will be understood that foot diagnostic device (200) may be used alone or in combination with either or both of remote computing device (300) and user mobile device (400).

Figure 2:
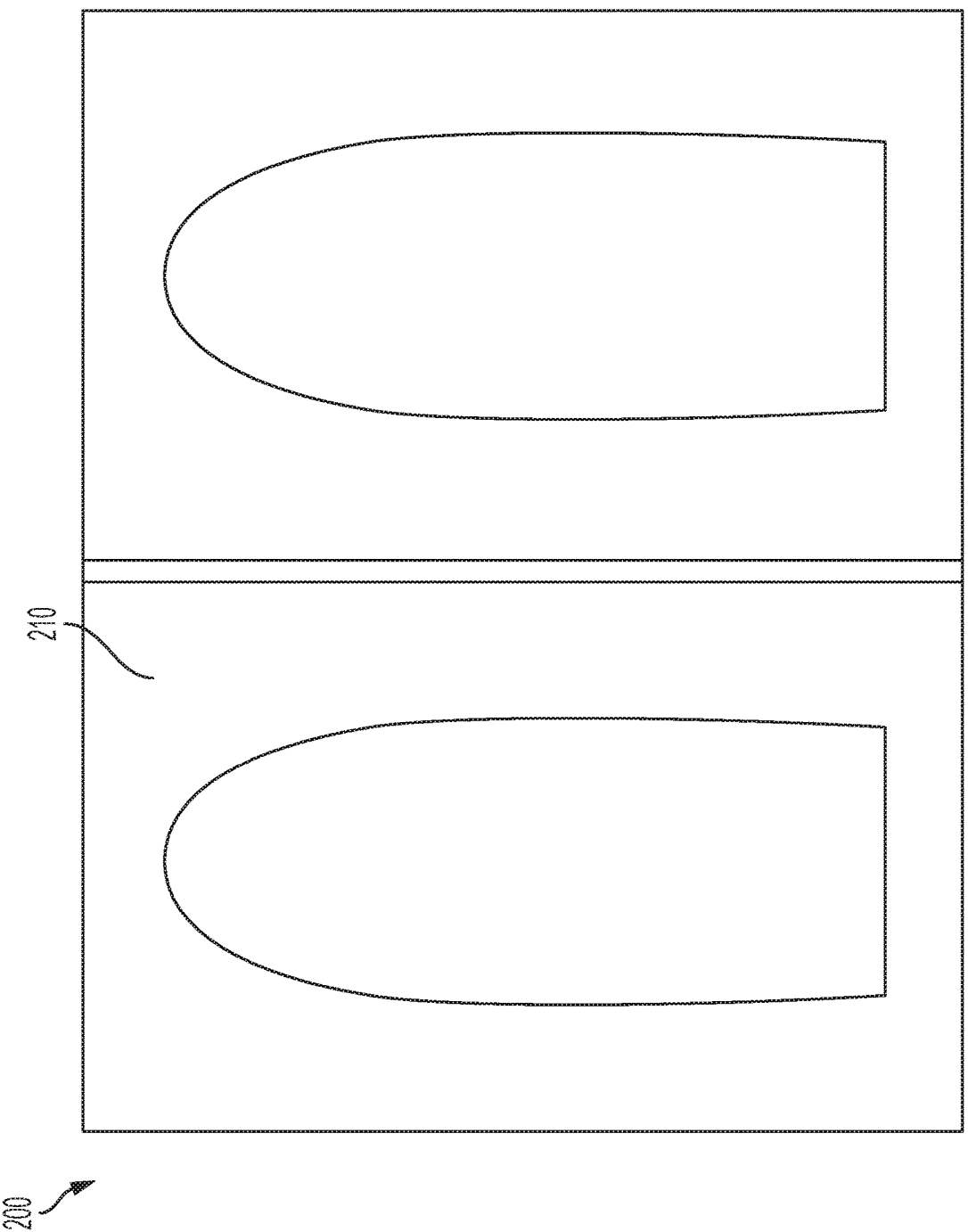
FIG. 2 shows a top down view of an exemplary foot diagnostic device of the exemplary monitoring system of FIG. 1.

Foot diagnostic device (200) as shown in FIG. 1 and FIG. 2 has the form of an enclosure that is sized and formed to fit a patient's feet. A patient's feet would rest within a foot base (210) of foot diagnostic device (200). A foot cover (220) then closes on the patient's feet when the diagnostic tests are to be performed. Foot diagnostic device (200) includes a microcomputer (280) for processing information collected by various sensors within foot diagnostic device (200).

As seen in FIG. 2, foot base (210) may be shaped to receive a foot of a patient or a user. In the exemplary version, foot base (210) includes space for both feet (left and right) of a user, but it will be understood that foot base (210) may be constructed to accommodate only a single foot as well. In some versions, foot base (210) and foot cover (220) need not be limited to a mechanical enclosure. It will be understood that foot base (210) and foot cover (220) could include a cloth, elastomeric, or otherwise flexible covering to a user's foot able to hold and position sensors against a user's feet. Foot diagnostic device (200) could also comprise a shoe-like form factor such that a user could wear a separate foot diagnostic device (200) on each foot like a shoe. Other variations will be appreciated as well in light of the disclosure herein.

Figure 3:
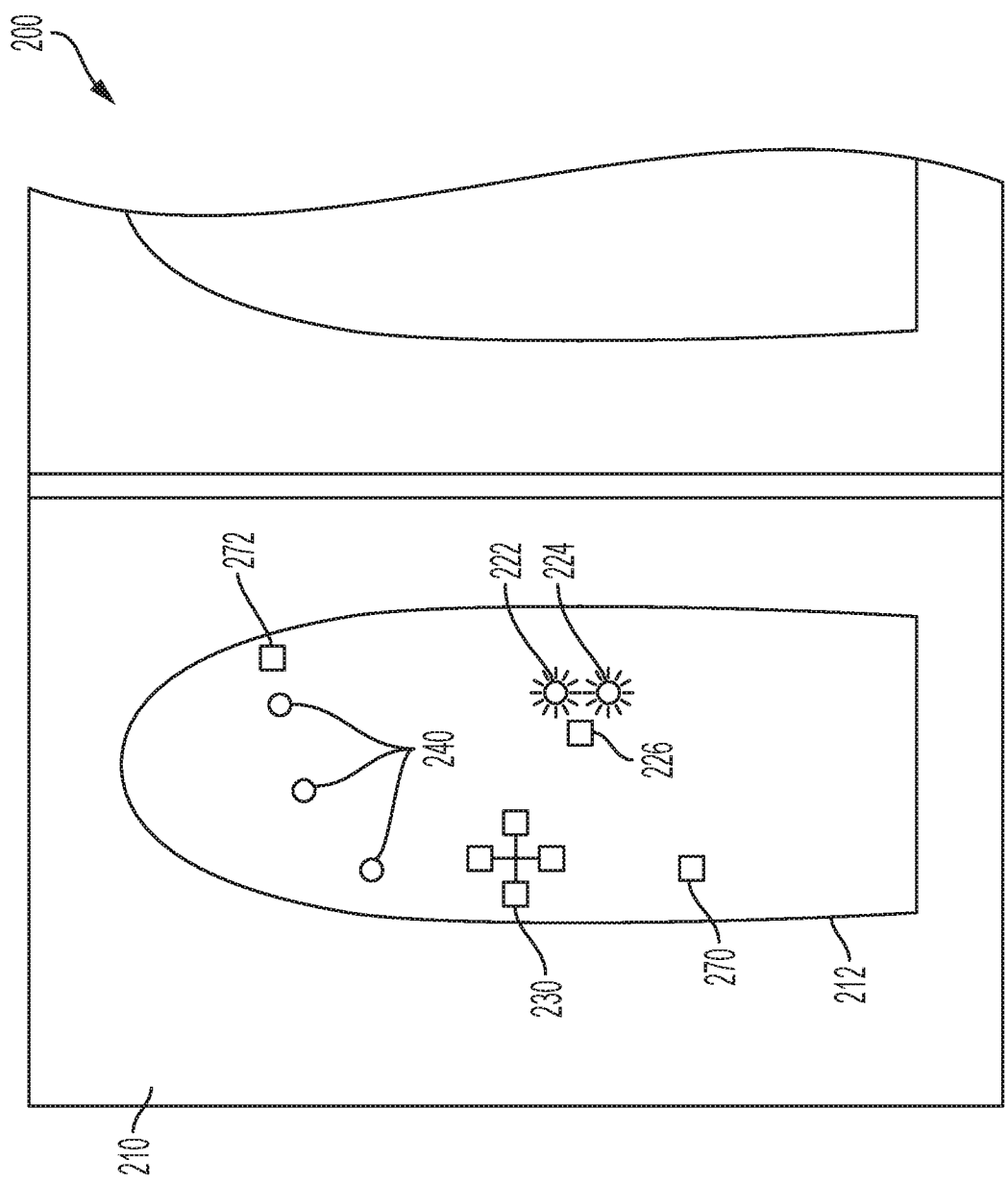
FIG. 3 shows a partial, top down view of the exemplary foot diagnostic device of FIG. 1 depicting the sensors contained in the foot diagnostic device.

Turning to FIG. 3, which shows a closer view of foot base (210). Foot base (210) has a foot bed (212) shaped or molded to fit the user's foot such that the user's foot can be positioned in a similar location within foot base (210) during each use of foot diagnostic device (200). In some instances, it may be desirable to take multiple diagnostic measurements of the user's foot. As such, it may be desirable to have the foot of the user positioned in the relatively same location each time the user places his or her foot in foot base (210).

Diagnostic Sensors

At a high level, foot bed (212) contains a collection of sensors able to measure different diagnostics of the user's foot. The different diagnostics may be measured independently from one another, or may be captured together. In some embodiments, the different diagnostics may even be captured in synchrony such that a user can see how the foot responds to different tests across a common variable of time. The results of the different diagnostic tests may be sent to a physician's office, or may be output to a device like a smartphone.

Turning now to some of the first elements in foot bed (212), a set of elements are configured such that oxygen concentration and blood flow may be measured or monitored. A photosensor array (230) works with an infrared (IR) source (222) and a visible light source (224) to measure or monitor oxygen saturation in the user's foot. In particular, IR source (222) and visible light source (224) emit IR and visible light, respectively. In the exemplary version, visible light source (224) emits a red colored light, but it will be understood that any color visible light may be used. Photosensor array (230) then measures the amount of IR and visible light received at the location of photosensor array (230) through the user's foot. Based on such information, an oxygen saturation may be determined. In the exemplary version, photosensor array (230) may include a set of photosensors arranged in a cross shaped pattern. It will be understood that other configurations of photosensor array (230) may be used as well. For instance, a single photosensor or other arrangements such as a line of photosensors or a square shaped arrangement, etc. may be used.

IR source (222) and visible light source (224) may also be used with a blood flow sensor (226). As IR and visible light is emitted from IR source (222) and visible light source (224), blood flow sensor (226) can measure the rate of blood flow through the user's foot. In the exemplary version, blood flow sensor (226) is located near IR source (222) and visible light source (224), but it will be understood that any suitable location for blood flow sensor may be used. In the exemplary version, blood flow sensor (226) may be located under the bridge of the foot placed in foot bed (212). In other versions, blood flow sensor (226) may be located in the middle of the foot, or multiple blood flow sensors (226) may be used to provide insight into blood flow through different portions of the foot.

Figure 4:
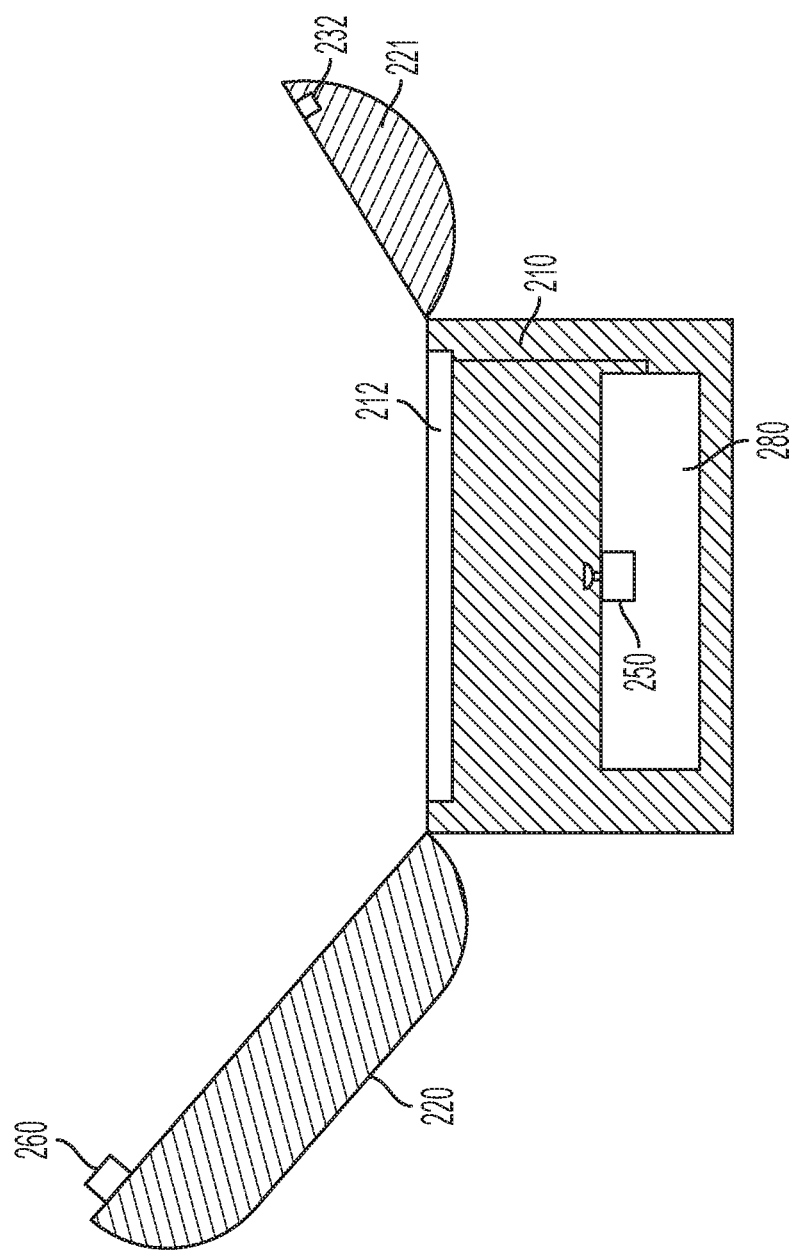
FIG. 4 shows a side, cross sectional view of the foot diagnostic device of FIG. 1.

Jumping briefly to FIG. 4, in some versions, at least one ankle blood flow sensor (232) is positioned at or around the ankle of the foot in order to detect blood flow traveling into the foot. In such a variation, ankle blood flow sensor (232) may be used to detect blood flow through the ankle while another blood flow sensor (226) may be used in another region of the foot. It will be understood that synthesizing data from one portion of the foot to another would enable a user or physician to understand the flow of blood from one portion of the foot to another (such as blood flow from the ankle to the rest of the foot). In other variations, comparisons may be done between blood flow at different parts of the foot by using multiple blood flow sensors (226) located at different locations in conjunction with ankle blood flow sensor (232).

Returning to FIG. 3, a single blood flow sensor (226) of a single size may be used, but variations may include having multiple blood flow sensors (226) of different sizes (such as one large and one small) as would be appropriate to detect blood flow through different portions of the foot. In the exemplary version, a photoplethysmography (PPG) sensor may be used to measure blood flow, but it will be appreciated that any type of sensor may be used for blood flow sensor (226).

Foot bed (212) may also contain a nerve stimulator (270) that works with neuropathy sensor (272) to determine nerve conductivity of a patient. Nerve stimulator (270) provides an electrical stimulus within the foot of the patient. Neuropathy sensor (272) then detects the electrical stimulus generated by nerve stimulator (270). As a result of coordinating the timing of starting a stimulus from nerve stimulator (270) and detecting the time it takes the stimulus to reach neuropathy sensor (272), one can determine, report on, and potentially detect the health of neurons active between nerve stimulator (270) and neuropathy sensor (272) based on the speed of propagation. Furthermore, in some instances where the characteristics of the electrical signal are known, it can be determined the quality of propagation of the signal traveling from nerve stimulator (270) to neuropathy sensor (272), which might provide further insight about nerve function in the user's foot.

Foot bed (212) further includes multiple muscle sensors (240). In the exemplary version, 3 muscle sensors (240) are shown, but it will be understood that any suitable number of sensors may be user. For instance, 10-20 muscle sensors may be used to detect muscle activity throughout the user's foot. Generally, it is understood that the more muscles are covered by muscle sensors (240), the more complete the information will be to determine the overall health of a user's foot muscles. Furthermore, the exemplary muscle sensors (240) are shown to be positioned near the bottom of the toes of a user, but in other versions, muscle sensors (240) may be positioned at any suitable location. For instance, they may be positioned in the arch of the foot, the bridge, the heel, the ankle, or any other suitable position that would enable monitoring of muscle functionality in the user's foot. In some instances, some muscle sensors (240) may be used to cover areas of muscle, while other muscle sensors (240) may be used to cover predominantly boney areas to detect or compare the health of muscles as the user flexes his or her feet. In the illustrated versions, muscle sensors (240) may comprise electromyogram sensors, but any sensors able to detect muscle activity may be used.

Structure of Foot Diagnostic Device

Turning now to FIG. 4, as described earlier, foot diagnostic device (200) comprises foot base (210), a first foot cover (220), and a second foot cover (221). It will be understood that first foot cover (220) and second foot cover (221) may be connected to foot base (210) through a hinged connection. As a result, once the user places his or her feet in foot bed (212), the first foot cover (220) and second foot cover (221) may close over the user's feet to allow foot diagnostic device (200) to perform a number of tests enabled by the various sensors previously discussed. In some versions, first foot cover (220) and second foot cover (221) may be connected to foot base (210) through a spring hinged connection such that if they are opened from the user's feet, first and second foot cover (220, 221) may further spring open. It will be understood that any suitable method of covering the user's feet and releasing first and second foot cover (220, 221) may be used.

FIG. 4 also shows a microcomputer (280) is in communication with foot bed (212), which may be used to capture information from the various sensors included in foot bed (212). For instance, microcomputer (280) may be programmed to send, receive, and/or process sensor data from photosensor array (230), blood flow sensor (226), muscle sensors (240), and neuropathy sensor (272). In addition, microcomputer (280) may be used to receive information from stimulus elements such as nerve stimulator (270), IR source (222), and visible light source (224). By receiving information about the various stimuli, it will be understood that such information may be synchronized with information received from any of photosensor array (230), blood flow sensor (226), muscle sensors (240), and neuropathy sensor (272), or combinations thereof.

Microcomputer (280) may have a variety of functionality to further extend the capabilities of foot diagnostic device (200). In some versions, microcomputer (280) may include communication hardware capable of wirelessly communicating with a number of devices. In some instances, microcomputer (280) may be used to initiate and propagate signals that can modulate or otherwise modify the functioning of one or more of the sensors in communication with microcomputer (280). Returning briefly to FIG. 1, in some instances, the communication protocol of microcomputer (280) may use wifi to connect to remote computing device (300) located at a physician's office. In other versions, microcomputer (280) may use bluetooth or wifi to connect to mobile device (400) to communicate results to the user. When microcomputer (280) connects to either mobile device (400) or remote computing device (300), it will be understood that an app may be interacted with by the user to either receive information regarding diagnostic test information from foot diagnostic device (200). Alternatively, an app may be used to initiate tests administered by foot diagnostic device (200).

Microcomputer (280) may also be used to intelligently synthesize data received from the various sensors of foot diagnostic device (200). For instance, microcomputer (280) may be able to multiplex and synchronize data received from multiple sensors as different diagnostics are measured from the user's foot, which may include storing and reporting historical diagnostic information. As a result, the user or physician may be able to view correlations between different diagnostic tests captured simultaneously or over time. In some instances, microcomputer (280) may simply output raw information from the different sensors of foot diagnostic device (200). In other instances, microcomputer (280) may output information based on an interpretation of the raw data. For instance, output from blood flow sensor (226) may be raw data such as the wavelength of either IR source (222) or visible light source (224) or may be interpreted to determine a corresponding blood flow within the user's foot.

In the illustrated version, a microcomputer (280) is used, but in other instances, a microcontroller, or any other suitable processing device may be used. For instance, a Raspberry Pi could be used in place of microcomputer (280) as an example of a specific type of microcomputer, but it will be understood that a full laptop or PC may be used as well.

Turning back to FIG. 4, in addition to microcomputer (280), a foot camera (250) is in communication with microcomputer (280). Foot camera (250) may comprise an IR camera, an RGB camera, or both. In some instances, foot camera (250) could include a digital SLR (DSLR), CMOS based, CCD based, polychromatic, monochromatic, microscopic, near infrared (NIR), polarized, and/or board cameras. It is further understood that foot camera (250) may utilize a variety of interfaces to communicate with microcomputer (280) or any other external device. For instance, foot camera (250) could use USB, Gigabit Ethernet (GigE), firewire, Bluetooth, wifi, or any other suitable communication method to transmit or receive data from microcomputer (280) or any other external device. It will be appreciated that foot bed (212) may be constructed of a material that may be transparent to foot camera (250) such that images from foot camera (250) can capture images from the bottom of the user's foot. Images from foot camera (250) may be used to correlate information captured by the other sensors in foot diagnostic device (200). For instance, an IR camera used for foot camera (250) may show warm spots in the foot. In conjunction with sensor data from blood flow sensor (226), the user or a physician could confirm that such warm spots are consistent with data output from blood flow sensor (226). In addition, in the event that there are multiple foot cameras (250) (e.g., one IR and one RGB), then the user or physician could also confirm that the visual health of the foot is healthy in addition to understanding whether the blood flow of the foot is normal.

While the above description discusses microcomputer (280) as being able to process the information, it will be understood that in some versions, microcomputer (280) may simply relay information to a remote computer or user mobile device such as the ones shown in FIG. 1 such that the mobile device or remote computer can process the information. In other versions, information may be directly sent to a server or cloud to perform analytics and processing of the information and communicate such information to a user's mobile device or a remote computer.

While in the illustrated version, there is foot camera (250) positioned underneath foot bed (212). It will be appreciated that more than one camera may be used and positioned in different places within foot diagnostic device (200). Some variations may include placing a foot camera (250) above the foot within foot diagnostic device (200) so that a user or physician can see the visible health of the top of the foot. It will be understood that other locations for foot camera (250) may be used to observe and determine overall foot health of the user.

FIG. 4 also shows a UV sanitizer (260), which functions to sanitize foot diagnostic device (200) between uses. UV sanitizer (260) generally comprises a UV light source able to sanitize contaminated surfaces. In the exemplary version, once the user is done using foot diagnostic device (200), UV sanitizer (260) may be activated for a period of 20-30 minutes or any other suitable amount of time to disinfect foot diagnostic device (200).

Multi Sensor Variation

Figure 5:
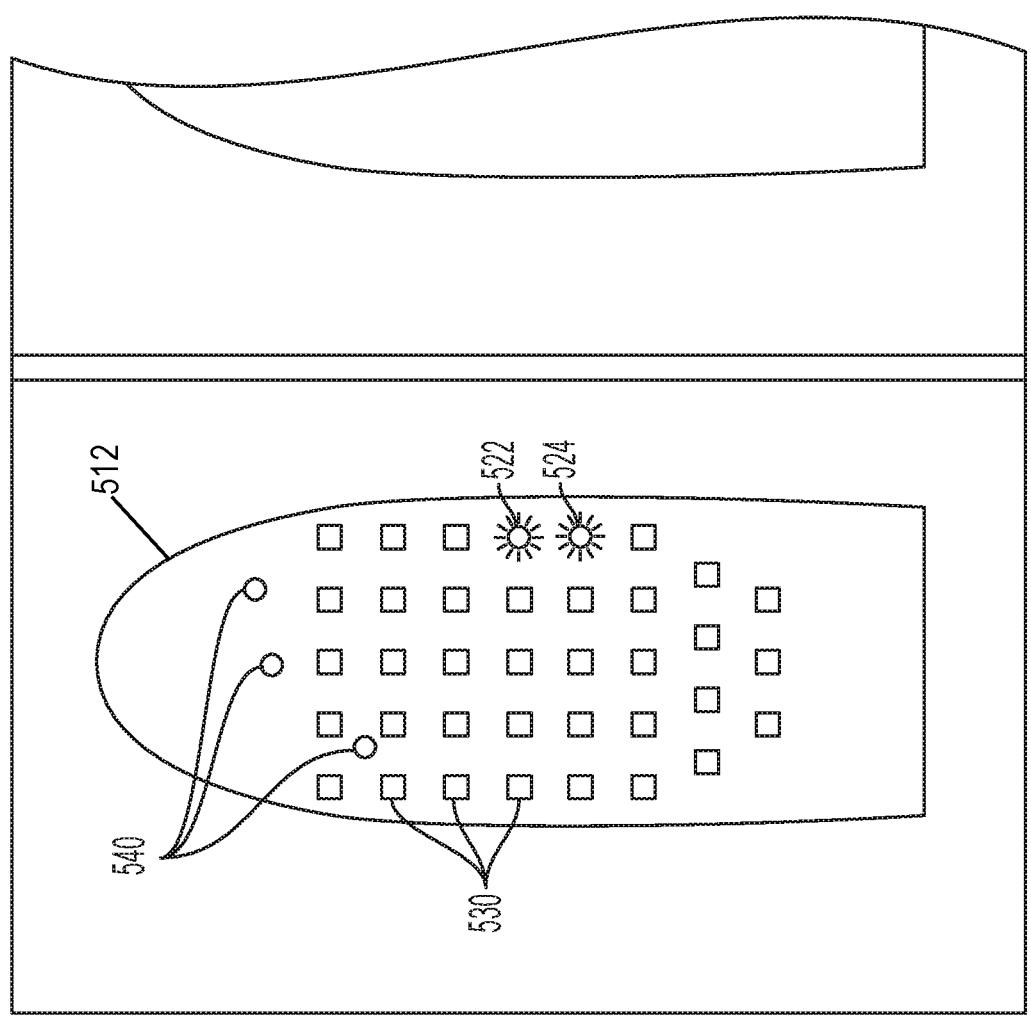
FIG. 5 shows a partial, top down view of an alternative version of the foot diagnostic device.

FIG. 5 shows a variation of foot bed (512) that includes an array of sensors (530) spanning the foot bed (512). As a result, more information from each sensor may be gathered, thereby increasing the resolution of sensor data captured from the user's feet in foot diagnostic device (200). As seen in FIG. 5, array of sensor (530) are spread out along the entire surface area of where a foot might be placed. Foot bed (512) includes an IR source (522) and a visible light source (524) similar to the same in FIG. 3. As a result of using a large array of sensors (530), this variation enables capturing propagation of IR or visible light throughout the foot of the user with great resolution. This variation also includes muscle sensors (540), which may be used to report on the overall health of the patient's muscles. The illustrated version envisions array of sensors (530) to be IR or visible light sensors to determine blood flow and concentration throughout the user's foot, but in other variations, array of sensors (530) may include muscle sensors, neuropathy sensors, or any of the previously discussed sensors or combinations thereof. As a result of providing array of sensors (530) throughout foot bed (512), the user could observe better resolution for any of the above discussed diagnostics.

In yet other versions, each of the sensors in array of sensors (530) may take multiple sensor readings over time and be combined with camera images taken by a camera similar to camera (250) of FIG. 4 via a microcomputer similar to microcomputer (280) of FIG. 4. As a result, the user may be able to view diagnostic information reported from many sensors (530) across the foot over a period of time. Such information may also be compared or correlated with other relevant information regarding the user's foot such as IR images, or visible images of the foot. Finally, through a microcomputer with network connectivity such as microcomputer (280) of FIG. 4, the information may be transmitted to a remote computer or user mobile device as depicted in FIG. 1.

App Interaction

Figure 6:
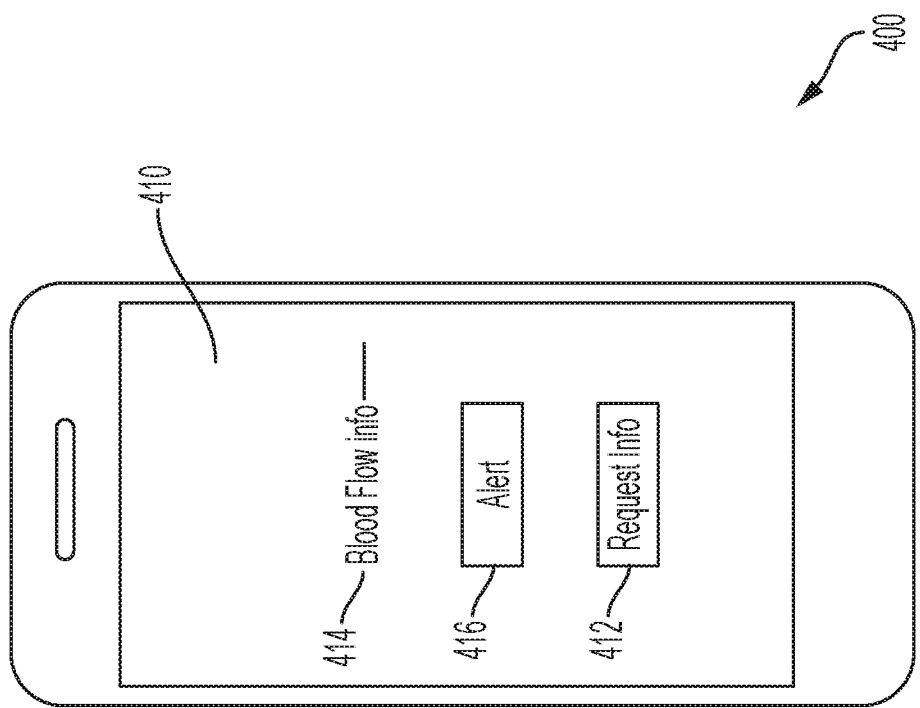
FIG. 6 shows a user mobile device of the exemplary monitoring system of FIG. 1.

FIG. 6 shows a user's mobile device (400) which may be used with foot diagnostic device (200). Microcomputer (280) of foot diagnostic device (200) may be used to wirelessly transmit information to user mobile device (400). Upon interacting with user mobile device (400), an app screen (410) can display relevant information as well as provide ways of interacting with foot diagnostic device (200).

For instance, diagnostic information (414) includes any relevant information provided via the sensors previously discussed for foot diagnostic device (200). In the illustrated version, a label for blood flow information (414) is shown, but it will be understood that information shown could include the raw sensor data but could also display calculated, derived, or inferred information based on the raw sensor data. For instance, in the context of blood flow information, either the raw data indicating the wavelength of the various blood flow sensors could be displayed or a derived number indicating the flow of blood through the user's foot may be shown.

In yet other versions, app screen (410) can show other diagnostic information from foot diagnostic device (200) including images taken by foot camera (250), as well as raw data or calculated information from any of the muscle or nerve sensors previously discussed. In addition, app screen (410) can display other data related to any of the diagnostic information discussed such as conditions for the various diagnostic tests, timing of different readings, and multiple readings from the various sensors shown over time.

App screen (410) can also include alert indicators (416) and diagnostic request keys (412). In the illustrated version, alert indicator (416) provides a visual or audio alert in the event that one of the diagnostic tests provides a reading that may be of concern. For instance, if the nerve propagation of a user is not as expected, if blood flow or oxygen saturation is poor, then alert indicator (416) may provide a visual alert or other suitable notification to the user. In the context of blood flow, it will be understood that an average blood flow of 2.4 mL/min may be considered healthy. As a result, as the blood flow of a user deviates from 2.4 mL/min, the user might be alerted through mobile device (400) that blood flow information from foot diagnostic device (200) is abnormal or needs further review. In other variations, a notification may be sent to the physician of the user to further assess the diagnostic information. In yet other variations, the application underlying app screen (410) may have AI algorithms able to perform machine learning over time based on the information provided by the user, thereby providing more intelligent recommendations and alerts. Such machine learning could be used in conjunction with larger data sets located either locally or remotely to provide machine learning based insights and learnings to the user based on the diagnostic information provided. Thus, immediate, AI-based feedback could be provided to the user via app screen (410) as a result of comparing readings from foot diagnostic device (200) to relevant data sets accumulated over time from the user or from other large sources of data with respect to blood flow or any other relevant type of diagnostic data.

In the context of oxygen saturation, it will be understood that 96-97% oxygen saturation in blood may be considered normal. As the oxygen saturation of the user deviates from the normal values, an alert may be sent to the user via alert indicator (416) or to the user's physician for further follow up.

Diagnostic request keys (412) comprise a user interface element that the user may interact with to perform any of the diagnostic tests in foot diagnostic device (200). As a result of tapping or otherwise interacting with diagnostic request keys (412), the user can start all or any of the tests in foot diagnostic device (200). As tests are being run, the information can then be sent to mobile device (400).

The subject matter described above is provided by way of illustration only and may not be construed as limiting. Various modifications and changes may be made to the subject matter described herein without following the example embodiments and applications illustrated and described, and without departing from the true spirit and scope of the present invention, which is set forth in the following claims.

What is claimed is:

1. A foot diagnostic device comprising:
    a housing having a base and a cover, the base and the cover being mechanically coupled to each other and operable to enclose a human foot;
    a foot bed formed in the base of the housing;
    an image capture device positioned within the housing such that the image capture device can capture image information comprising an image or video of a user's foot placed in the foot bed;
    a sensor array positioned within the foot bed, the sensor array comprising:
    a nerve stimulus and a nerve sensor,
    a muscle stimulus and a muscle sensor,
    a light source and an oxygen saturation sensor, and
    a blood flow sensor; and
    a microcomputer in communication with the nerve sensor, the muscle sensor, the oxygen saturation sensor, and the blood flow sensor, wherein the microcomputer is operable to collect diagnostic information received from the nerve sensor, the muscle sensor, the oxygen saturation sensor, and the blood flow sensor such that multiple kinds of the diagnostic information are captured simultaneously and thereafter can transmit the multiple kinds of the diagnostic information in real time to a remote location, wherein the microcomputer is operable to control the functions of one or more of the nerve sensor, the muscle sensor, the oxygen saturation sensor, or the blood flow sensor and wherein the microcomputer is operable to collect the image information from the image capture device such that the image capture information corresponds to the multiple kinds of the diagnostic information, wherein the microcomputer is further operable to transmit the image capture information and the multiple kinds of the diagnostic information recorded such that the image capture information and the multiple kinds of the diagnostic information are displayed simultaneously at similar locations on the foot.

2. The foot diagnostic device of claim 1, the oxygen saturation sensor comprising a cross-shaped arrangement of at least four light sensors positioned within the foot bed.

3. The foot diagnostic device of claim 1, wherein the cover comprises a first portion and a second portion, the first portion and the second portion are attached to the base via a hinge, wherein the first portion is operable to rotate and cover the anterior portion of a user's foot, wherein the second portion is operable to rotate and cover the posterior portion of a user's foot.

4. The foot diagnostic device of claim 1, wherein the microcomputer further comprises wireless communication hardware operable to wirelessly communicate with a remote location.

5. The foot diagnostic device of claim 4, wherein the wireless communication hardware is operable to communicate wirelessly to an application installed on a mobile device.

6. The foot diagnostic device of claim 5, wherein the application on the mobile device is configured to display diagnostic information captured by the sensor array.

7. The foot diagnostic device of claim 5, wherein the application on the mobile device is configured to initiate diagnostic tests using the sensor array.

8. The foot diagnostic device of claim 4, wherein the wireless communication hardware transmits information to a physician's office in the event that any diagnostic information captured by the sensor array is determined to be abnormal.

9. The foot diagnostic device of claim 1, further comprising an ultra violet (UV) light connected to the housing, wherein the UV light is operable to sanitize the foot bed.

10. The foot diagnostic device of claim 1, wherein at least one of the nerve sensor, the muscle sensor, the oxygen saturation sensor, and the blood flow sensor comprises a plurality of individual sensor units positioned to span the entire surface area of the foot bed.

11. The foot diagnostic device of claim 1, wherein the image capture device is positioned such that the image capture device can image substantially the entire surface area of a user's foot in contact with the foot bed, wherein the image capture device is further positioned to image a portion of an ankle of a user's foot.

12. The foot diagnostic device of claim 11, wherein the image capture device includes one or more or an infrared camera, a digital SLR camera, a CMOS based camera, a CCD based camera, a polychromatic camera, a monochromatic camera, a microscopic camera, a near infrared camera, a polarized camera, or a board camera.

\* \* \* \* \*